United States Patent [19]

Davies et al.

[11] 4,160,017

[45] * Jul. 3, 1979

[54] HERBICIDAL COMPOSITIONS

[75] Inventors: George E. Davies, Wilmslow; David M. Foulkes, Henley-on-Thames, both of England

[73] Assignee: Imperial Chemical Industries Limited, London, England

[*] Notice: The portion of the term of this patent subsequent to Sep. 6, 1994, has been disclaimed.

[21] Appl. No.: 830,765

[22] Filed: Sep. 6, 1977

Related U.S. Application Data

[63] Continuation of Ser. No. 716,801, Aug. 23, 1976, Pat. No. 4,046,552.

[30] Foreign Application Priority Data

Apr. 15, 1976 [GB] United Kingdom ............... 15584/76

[51] Int. Cl.$^2$ ...................... A61K 31/395; A01N 9/22
[52] U.S. Cl. ........................................... 424/10; 71/92; 71/94; 424/2; 424/251

[58] Field of Search ................. 424/2, 251, 10; 71/92, 71/94

[56] References Cited

U.S. PATENT DOCUMENTS

| | | | |
|---|---|---|---|
| 3,689,488 | 9/1972 | Dukes | 544/263 |
| 3,920,443 | 11/1975 | Drewe et al. | 71/94 |
| 3,929,449 | 12/1975 | Hedrich | 424/10 |
| 4,075,005 | 2/1978 | Knowles et al. | 71/94 |

OTHER PUBLICATIONS

Davies et al., Nature New Biology, vol. 234, pp. 50–51, (1971).

*Primary Examiner*—Joseph Paul Brust
*Attorney, Agent, or Firm*—Cushman, Darby & Cushman

[57] ABSTRACT

A method of avoiding the toxifying effect of a salt of a herbicidal bipyridylium quaternary cation ingested by a human which comprises administering to said human an emetically effective amount of an s-triazolo[1,5-a]pyrimidine derivative.

1 Claim, No Drawings

HERBICIDAL COMPOSITIONS

This is a continuation of application Ser. No. 716,801, filed Aug. 23, 1976, now U.S. Pat. No. 4,046,552.

This invention relates to herbicidal compositions containing a herbicidal bipyridylium quaternary salt as an active ingredient.

Over the years, a wide range of pesticides has been developed for agricultural use in the control of fungal and insect pests and weeds. While these substances are necessarily toxic to certain forms of life, when used with due care and in accordance with governmentally approved codes of practice, they present no hazard to human life. However, in spite of efforts to encourage those concerned with pesticides to adopt safe handling practices, instances of misuse of pesticides do occur. One particular unsafe practice in the case of liquid pesticides is for an operator to transfer a small amount of the concentrated pesticide to a domestic container such as a beverage bottle for subsequent use at home. The risk attached to these practices is of course that a child or incautious adult coming upon the bottle may swallow the contents with possibly serious consequences.

We have now found it possible to reduce the likelihood of serious consequences of such accidental swallowing by induction of emesis. This can result in some cases in the rapid removal of the pesticidal composition from the stomach and digestive tract before lethal amounts of the pesticide can be assimilated by the body.

We have further discovered that the admixture of a known triazolo[1,5-a]pyrimidine derivative of formula (I), as specified hereinafter, to a herbicidal bipyridylium quaternary salt in a herbicidal composition produces a composition which if swallowed tends to induce emesis, and thereby, expulsion of the composition.

According to the invention there is provided a herbicidal composition of reduced health hazard comprising a salt of a herbicidal bipyridylium quaternary cation and an effectively emetic amount of a s-triazolo-[1,5-a]-pyrimidine derivative of the formula:

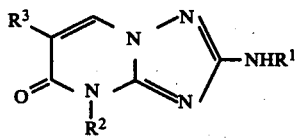

(I)

wherein $R^1$ is hydrogen, a $C_{1-4}$ alkyl radical, or a COOEt radical, $R^2$ is a $C_{1-4}$ alkyl radical or an allyl radical, and $R^3$ is a $C_{1-4}$ alkyl radical; and addition salts thereof. The s-triazolo[1,5-a]pyrimidine ring structure is numbered as shown below:

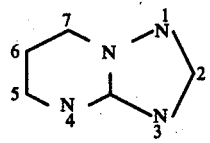

Particular derivatives of 5-oxo-4,5-dihydro-s-triazolo[1,5-a]pyrimidine of use in the practice of the invention are:
6-methyl-4-n-propyl-2-n-propylamino-
2-amino-6-methyl-4-allyl-
2-amino-4,6-di-n-propyl-
2-ethoxycarbonylamino-6-methyl-4-n-propyl- An especially useful triazolo-pyrimidine for use in the compositions of the invention is 2-amino-6-methyl-5-oxo-4-n-propyl-4,5-dihydro-s-triazolo[1,5-a]pyrimidine (II).

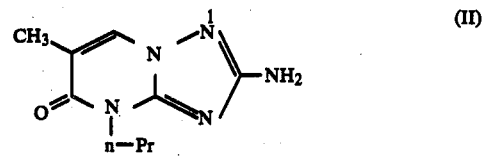

(II)

Preferred herbicidal bipyridylium quaternary salts for use in the compositions of the invention are those of the following formulae:

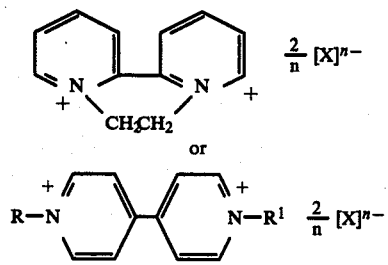

wherein R and $R^1$, which may be the same or different, stand for alkyl radicals of from 1 to 4 carbon atoms which may be substituted by hydroxyl, halogen, carboxyl, alkoxy, alkylcarbonyl, alkoxycarbonyl, carbamoyl or N-substituted carbamoyl; $[X]^{n-}$ represents an anion and n is an integer from 1 to 4 inclusive.

Particularly preferred herbicidal bipyridylium quaternary salts are those listed below:
1,1-dimethyl-4,4'-bipyridylium di(methylsulphate) (paraquat dimethosulphate)
1,1'-ethylene-2,2'-bipyridylium dibromide (diquat dibromide)
1,1'-dimethyl-4,4'-bipyridylium dichloride (paraquat dichloride)
1,1'-di-2-hydroxyethyl-4,4'-bipyridylium dichloride
1-(2-hydroxyethyl-1'-methyl-4,4'-bipyridylium dichloride
1,1'-di-carbamoylmethyl-4,4'-bipyridylium dichloride
1,1'-bis-N,N-dimethylcarbamoylmethyl-4,4'-bipyridylium dichloride
1,1'-dimethyl-4,4'-bipyridylium sulphate (paraquat sulphate)
1,1'-bis-N,N-diethylcarbamoylmethyl-4,4'-bipyridylium dichloride
1,1'-diacetonyl-4,4'-bipyridylium dichloride
1,1'-diethoxycarbonylmethyl-4,4'-bipyridylium dibromide
1,1'-diallyl-4,4'-bipyridylium dibromide The names in brackets alongside some of the compounds in the above list are the accepted common names for the cationic portion of these compounds. Thus 'paraquat' is the common name for the 1,1'-dimethyl-4,4'-bipyridylium cation. Paraquat is a particularly preferred bipyridylium compound for use in the compositions of the invention. A particularly preferred anion $[X]^{n-}$ is the chloride anion, for reasons of convenience and economy, but any anion which gives rise to a conveniently water-soluble salt may be used if desired. The herbicidal action is due solely to the cation and for this reason the concentration of a herbicidal bipyridylium salt compositions is frequently given in terms of the cation alone. The amount of herbicidal bipyridylium quaternary salt present in the compositions of the invention is generally from 1.0 to 99.9% by weight.

The compositions of the invention may be solids, e.g. granules, or liquids, e.g. aqueous solutions.

In a preferred aspect the invention provides a concentrated herbicidal composition comprising an aqueous solution of a salt of a herbicidal bipyridylium quaternary cation and an effectively emetic amount of a triazolo-pyrimidine as hereinbefore defined. Preferably the herbicidal bipyridylium quaternary cation is paraquat.

The amount of herbicidal bipyridylium quaternary cation present in the aqueous solution is preferably from 0.05 to 4.0 pounds per Imperial gallon (50 grams to 400 grams per liter).

Preferably the composition also comprises a surface active agent.

Surface-active agents may be cationic, non-ionic or anionic. Generally speaking cationic and non-ionic surface-active agents are preferred to anionic surface-active agents for use in the compositions of the invention, since the latter may interact undesirably with the bipyridylium quaternary salt in the compositions. Examples of non-ionic surface-active agents for use in the compositions of the invention include the condensation products of ethylene oxide with alkyl phenols such as octylphenol, nonylphenol and octylcresol. Other non-ionic agents are the partial esters derived from long chain fatty acids and hexitol anhydrides, for example sorbitan monolaurate; the condensation products of the said partial esters with ethylene oxide; and the lecithins. Examples of cationic surface-active agents include quaternary salts and condensates of ethylene oxide with amines, for example the substances sold under the Trade Mark "Ethomeen", "Ethoduomeen", "Duoquad" and "Arquad".

Particularly preferred surface-active agents are the combinations of surface-active agents described in U.K. Pat. No. 998,264 for use in formulations of herbicidal bipyridylium quaternary salts.

The preparation of the triazolo-pyrimidines (I) has been described in U.S. Pat. Nos. 3,689,488 and 3,773,949; which description is herein incorporated by reference.

The emetic properties of the composition are primarily determined by the amount of triazolo-pyrimidine it contains. In deciding the most appropriate amounts of triazolo-pyrimidine to use in any composition, regard must be had to the efficacy of the triazolo-pyrimidine relative to the toxicity of the herbicide. The amount of triazolo-pyrimidine to be included is preferably such that a sample of the composition containing a potentially lethal dose of herbicide contain sufficient of the triazolo-pyrimidine to give it an emetic action. However, clearly neither lethal doses nor emetic doses can be directly measured in man; they can only be inferred from animal data.

Compositions according to the invention preferably contain from 0.1 to 5 parts by weight of the triazolo-pyrimidine (I) per 100 parts of the herbicidal bipyridylium quaternary cation. Conveniently the amount of the triazolo-pyrimidine (I) used is 0.25 to 2.0 parts per 100 parts of herbicidal bipyridylium quaternary cation.

Concentrated aqueous formulations of the invention are corrosive. They must be handled with care, to avoid splashing on the eyes or skin, and they should not be allowed to come into contact with corrodeable metals prior to dilution.

The compositions according to the invention may also comprise coloured dyestuff or pigment compounds. Examples of such compounds are "Monastral Blue BNV Paste" and "Lissamine Turquoise VN 150".

The compositions according to the invention may also comprise a stenching agent. Examples of such stenching agents are alkyl pyridines as described in U.S. Pat. No. 3,920,443; which description is incorporated herein by reference.

If desired, the triazolo-pyrimidines (I) may be incorporated in thixotropic formulations of herbicidal quaternary salts. In particular the triazolo-pyrimidines (I) may be incorporated in the formulations of herbicidal bipyridylium quaternary salts described in our U.K. patent Specification No. 1,395,502; which description is incorporated herein by reference. These formulations comprise an aqueous solution of a herbicidal bipyridylium quaternary salt containing a gelling agent, for example finely divided silica, or a combination of the xanthan gum sold under the trade name "Kelzan" with sodium metaborate. Xanthan gum is a complex polysaccharide.

The composition according to the invention may also comprise a herbicide other than a herbicidal bipyridylium quaternary salt as hereinbefore defined. Examples of such herbicides are:

Amides (e.g. N,N-diallylchloroacetamide, 3,4-dichloropropionanilide, N-(3-chloro-4-methyl-phenyl)-2-methylpentamide).

Carbamates (e.g. Isopropyl-N-phenylcarbamate, isopropyl-N-(3-chlorophenyl)carbamate, 4-chloro-2 but-2-ynyl-N-(3-chlorophenyl)carbamate, 2-chloral-lyl-N,N-diethyl-dithiocarbamate).

Ureas/anilides (e.g. N,N'-di-(2,2,2-trichloro-1-hydroxyethyl)urea, 3,4-dichloroacetanilide, O-chloroisobutyranilide, α-bromo-3,4-dichloroacetanilide, 3,4-dichloroformanilide, 2-acetamido-3-chlorotoluene).

Diazines (e.g. 3,4,5,6-tetrahydro-3,5-dimethyl-2-thio-2H-1,3,5-thiadiazine, 5-bromo-3-isopropyl-6-methyluracil, 5-amino-4-chloro-2-phenyl-3-pyridazone, 1,2,3,6-tetrahydro-3,6-dioxopyridazine).

Triazines (e.g. 2-chloro-4,6-bisethylamino-1,3,5-triazine, 2-chloro-4-ethylamino-6-isopropylamino-1,3,5-triazine, 2-chloro-4,6-bisisopropylamino-1,3,5-triazine, 4-ethylamino-6-isopropylamino-2-methoxy-1,3,5-triazine, 4,6-bisisopropylamino-2-methoxy-1,3,5-triazine).

The inclusion of the triazolo-pyrimidine (I) in compositions according to the invention has, in most cases, no significant adverse effect upon the herbicidal activity of the compositions. The invention is illustrated by the following Examples.

EXAMPLE 1

This Example illustrates a composition according to the invention which comprises 2-amino-6-methyl-5-oxo-4-n-propyl-4,5-dihydro-s-triazolo[1,5-a]pyrimidine (II) in aqueous solution.

| Ingredients | % w/v |
| --- | --- |
| Paraquat concentrate | x |

-continued

| Ingredients | % w/v |
| --- | --- |
| (II) | 0.05 |
| Water | to 100 ml |
| (where x gives 200 ± 5 g/liter paraquat cation) | |

Paraquat concentrate is a solution of paraquat dichloride containing 25% to 30% by weight of 1,1'-dimethyl-4,4'-bipyridylium cation. The amount specified in the table above was sufficient to give a composition containing 20% by weight of paraquat cation. The composition was prepared by simple agitation of the ingredients together.

EXAMPLE 2

This Example illustrates a composition according to the invention which comprises the triazolo-pyrimidine (II) in aqueous solution. The composition comprises the following ingredients.

| Ingredients | % w/v |
| --- | --- |
| Paraquat concentrate | x |
| Sodium metaborate | 1.3 |
| Sodium benzoate | 2.0 |
| Lissapol NX | 1.1 |
| DS 4392 | 4.1 |
| Silcolapse 5000 | 0.06 |
| (II) | 0.05 |
| Water | to 100 ml |
| (where x gives 200 ± 5 g/liter paraquat cation) | |

"Lissapol" NX is a Trade Mark for a surface-active agent comprising a condensate of from 7 to 8 molar proportions of ethylene oxide with 1 molar proportion of p-nonylphenol.

DS 4392 is a code number for a surface-active agent comprising a mixture of amines derived from soya bean fatty acids condensed with approximately 15 molar proportions of ethylene oxide.

"Silcolapse" is a Trade Mark for an anti-foaming agent comprising a silicone derivative.

The composition described above was prepared by simple agitation of the ingredients together.

EXAMPLE 3

This Example illustrates a composition according to the invention which comprises a gelling agent in addition to the triazolo-pyrimidine (II). The composition comprises the following ingredients.

| Ingredients | Amount in Grams |
| --- | --- |
| Paraquat concentrate | x |
| "Kelzan" | 0.4 (added as 1% solution in water) |
| Sodium metaborate | 0.014 |
| Lissapol NX | 1.1 |
| DS 4392 | 4.1 |
| (II) | 0.05 |
| Silcolapse 5000 | 0.01 |
| Water | to 100 ml |
| (where x gives 200 ± g/liter paraquat ion) | |

The composition described above was prepared by simple agitation of the ingredients together and was sufficiently fluid when prepared to be poured into containers. On standing for 15 to 20 minutes the composition formed a gel and was not pourable unless vigorously shaken.

EXAMPLE 4

This Example illustrates a dry free flowing granular composition which is both stable in storage and is readily convertible into an aqueous solution for application as a spray.

A solution was made up having the following composition in which percentages are by weight.

| | |
| --- | --- |
| Paraquat dichloride | 33.0 |
| 2-amino-6-methyl-5-oxo-4-n-propyl-4,5-dihydro-s-triazolo[1,5-a]pyrimidine (II) | 0.1 |
| Sodium metaborate | 2.5 |
| Potassium phosphate | 1.6 |
| Lissapol NX | 24.0 |
| Water | 38.8 |
| | 100 |

310 gms of the above solution were then added in a thin stream to 690 gms of dried magnesium sulphate contained in the bowl of a HOBART C.E. 100 dough mixer ("HOBART" is a Registered Trade Mark). The resulting product which was dry was then passed through a granulating machine and finally agitated in a sieve having 30 meshes per linear inch to remove dust. The resulting granules had a size of at least 0.9 mm and possessed a solution rate of 150 seconds.

EXAMPLE 5

This Example illustrates a composition according to the invention which comprises 2-amino-6-methyl-5-oxo-4-n-propyl-4,5-dihydro-s-triazolo[1,5-a]pyrimidine (II) and a stenching agent in aqueous solution.

| Ingredients | % w/v |
| --- | --- |
| Paraquat concentrate | x |
| n-valeric acid | 1.0 |
| II | 0.05 |
| DS 4392 | 4.0 |
| Silcolapse | 0.01 |
| Lissapol NX | 1.0 |
| Water | to 100 mls |
| (where x gives 200 g/l paraquat ion). | |

The compositions described above was prepared by simple agitation of the ingredients together.

EXAMPLE 6

This Example illustrates a composition according to the invention which comprises 2-amino-6-methyl-5-oxo-4-n-propyl-4,5-dihydro-s-triazolo[1,5-a]pyrimidine (II) in a thickened, coloured, aqueous solution.

| Ingredients | % w/v |
| --- | --- |
| Paraquat concentrate | x |
| Synperonic 2 | 2.5 |
| Synperonic 16 | 2.5 |
| Nansa 1106 | 8.5 |
| Monastral BNVS Paste | 1.0 |
| Pyridine Base | 1.0 |
| II | 0.05 |
| Water | to 100 mls |
| (where x gives 200 g/l paraquat ion). | |

"Synperonic" and "Nansa" are Trade Marks. Synperonic 2 is a condensation product of a mixture of 67% $C_{13}$ and 33% $C_{15}$ aliphatic alcohols with two equivalents of ethylene oxide. Synperonic 16 is a condensation product of a mixture of 67% $C_{13}$ and 33% $C_{15}$ aliphatic alcohols with sixteen equivalents of ethylene oxide. Nansa 1106 is sodium dodecyl (substantially $C_{12}$ straight chain) benzene sulphonate. Monastral BNVS paste is a dispersion comprising 15% w/v copper phthalocyanine pigment in water. Pyridine base is a mixture comprising substantially basic alkyl pyridines.

EXAMPLE 7

This Example illustrates a composition according to the invention which comprises 2-amino-6-methyl-5-oxo-4-n-propyl-4,5-dihydro-s-triazolo[1,5-a]pyrimidine (II) in aqueous solution.

| Ingredients | % w/v |
|---|---|
| diquat dibromide | x |
| sodium molybdate | 0.18 |
| potassium phosphate (as a mixture of dipotassium hydrogen phosphate and potassium dihydrogen phosphate) | 2.75 |
| (II) | 0.05 |
| water | to 100 ml |
| (where x gives 140 ± 5 g/l diquat ion). | |

Diquat ion is 1,1'-ethylene-2,2'-bipyridylium cation. The composition described above was prepared by simple agitation of the ingredients together, and had a pH of 6.5±0.3.

EXAMPLE 8

This Example illustrates a composition according to the invention which comprises 2-amino-6-methyl-5-oxo-4-n-propyl-4,5-dihydro-s-triazolo[1,5-a]pyrimidine (II) in aqueous solution.

| Ingredients | % w/v |
|---|---|
| Morfamquat dichloride | x |
| II | 0.05 |
| water | to 100 mls |
| (where x gives 300 ± 5 g/l morfamquat ion). | |

Morfamquat ion is 1,1'-bis(3,5-dimethylmorpholinocarbonylmethyl)-4,4'-bipyridylium ion. The composition described above was prepared by simple agitation of the ingredients together.

EXAMPLE 9

This Example illustrates a composition according to the invention which comprises 2-amino-6-methyl-5-oxo-4-n-propyl-4,5-dihydro-s-triazolo[1,5-a]pyrimidine (II) in aqueous solution.

| Ingredients | % w/v |
|---|---|
| 1,1'-bis(diethylcarbamoylmethyl)-4,4'-bipyridylium dichloride | x |
| Tween 20 | 8 |
| (II) | 0.05 |
| water | to 100 mls |

(where x gives 200±5 g/l 1,1'-bis(diethylcarbamoylmethyl)-4,4'-bipyridylium ion). The composition described above was prepared by simple agitation of the ingredients together.

"Tween" is a Trade Mark. Tween 20 is a condensation product of one mole of sorbitan monolaurate with twenty moles of ethylene oxide.

EXAMPLE 10

This Example illustrates a composition according to the invention which comprises 2-n-propylamino-6-methyl-5-oxo-4-n-propyl-4,5-dihydro-s-triazolo[1,5-a]pyrimidine in aqueous solution.

| Ingredients | % w/v |
|---|---|
| Paraquat concentrate | x |
| 2-n-propylamino-6-methyl-5-oxo-4-n-propyl-4,5-dihydro-s-triazolo [1,5-a] pyrimidine | 0.05 |
| Water | to 100 ml |
| (where x gives 200 ± 5 g/liter paraquat cation | |

EXAMPLE 11

This Example illustrates a composition according to the invention which comprises 2-amino-5-oxo-4,6-di-n-propyl-4,5-dihydro-s-triazolo[1,5-a]pyrimidine in aqueous solution.

| Ingredients | % w/v |
|---|---|
| Paraquat concentrate | x |
| 2-amino-5-oxo-4,6-di-n-propyl-4,5-dihydro-s-triazolo [1,5-a]-pyrimidine | 0.05 |
| Water | to 100 ml |
| (where x gives 200 ± 5 g/liter paraquat cation) | |

EXAMPLE 12

This Example illustrates a composition according to the invention which comprises 2-ethoxycarbonylamino-6-methyl-5-oxo-4-n-propyl-4,5-dihydro-s-triazolo[1,5-a]pyrimidine in aqueous solution.

| Ingredients | % w/v |
|---|---|
| Paraquat concentrate | x |
| 2-ethoxycarbonylamino-6-methyl-5-oxo-4-n-propyl-4,5-dihydro-s-triazolo [1,5-a] pyrimidine | 0.05 |
| Water | to 100 ml |
| (where x gives 200 ± 5 g/liter paraquat cation) | |

EXAMPLE 13

This Example illustrates a composition according to the invention which comprises 2-amino-6-methyl-5-oxo-4-allyl-4,5-dihydro-s-triazolo[1,5-a]pyrimidine in aqueous solution.

| Ingredients | % w/v |
|---|---|
| Paraquat concentrate | x |
| 2-amino-6-methyl-5-oxo-4-allyl-4,5-dihydro-s-triazolo [1,5-a]-pyrimidine | 0.05 |
| Water | to 100 ml |
| (where x gives 200 ± 5 g/liter paraquat cation) | |

EXAMPLE 14

This Example illustrates the reduced likelihood of serious consequences resulting from the ingestion of a herbicidal composition according to the invention.

With monkeys. Male cynomolgus monkeys (*Macaca fasicularis*), body weights in the range 3.5–5 kg, were used.

Test 1

Eight monkeys were dosed with a herbicidal bipyridylium quaternary salt composition as specified below containing 100 mg paraquat ion/kg body weight.

The required amount of a composition comprising:

| Ingredients | % w/v |
|---|---|
| paraquat concentrate | x |
| Lissapol NX | 1.1 |
| DS 4392 | 4.1 |
| Silcolapse 5000 | 0.01 |
| Water | to 100 ml |
| (where x gives 200 ± 5 g/l paraquat ion.) | | was diluted with water to 20 ml to give 100 mg paraquat ion/kg body weight, and to which was added 10 g of 'COMPLAN'. 'COMPLAN' is a Trade Mark for a carboxymethyl cellulose.

All eight of the monkeys died.

Test 2

Eight monkeys were dosed with a composition according to the invention comprising the same amount of the same composition (giving 100 mg paraquat ion/kg body weight) as specified in Test 1 plus 2-amino-6-methyl-5-oxo-4-n-propyl-4,5-dihydro-s-triazolo[1,5-a]pyrimidine (2 mg/kg body weight).

Only two of the monkeys died. The six animals that survived all vomited in the first hour after dosing.

Test 3

Test 1 was repeated with four monkeys. All the monkeys died within 3–4 days.

Test 4

Test 2 was repeated with four monkeys and carried out at the same time as test 3.

All the monkeys vomited; two about 20 minutes after dosing, one after approximately 45 minutes, and one after approximately 8 hours. The three monkeys which vomited early survived. The monkey which vomited later died.

With dogs. Male beagle dogs, body weight in the range 9–12 kg were used.

Test 5

Four dogs were dosed with a herbicidal bipyridylium quaternary salt composition as specified below at a rate of 20 mg paraquat ion/kg body weight.

| Ingredients | % w/v |
|---|---|
| Paraquat concentrate | x |
| Water | to 50 ml |

To this solution was added 6 g 'COMPLAN'.
(x to give 20 mg paraquat ion/kg body weight).

Three out of four of the dogs died within the first week of dosing.

Test 6

Four dogs were dosed with a composition according to the invention comprising the same amount of the same composition (giving 20 mg paraquat ion/kg body weight) as specified in Test 5 plus 2-amino-6-methyl-5-oxo-4-n-propyl-4,5-dihydro-s-triazolo[1,5-a]pyrimidine (3 mg/kg body weight). All of the dogs vomited within an hour of being dosed and none of them died.

Test 7

Test 5 was repeated but with the composition comprising 30 mg paraquat ion/kg body weight. Three out of the four dogs died.

Test 8

Test 6 was repeated but with the composition comprising 30 mg paraquat ion/kg body weight. All of the dogs vomited within an hour of being dosed and none of them died.

Test 9

Test 6 was repeated but with the composition comprising 2 mg of 2-amino-6-methyl-5-oxo-4-n-propyl-4,5-dihydro-s-triazolo[1,5-a]pyrimidine/kg body weight. All four dogs vomited within 15 minutes and survived.

EXAMPLE 14

This Example illustrates the emetic potency of several members of the s-triazolo-[1,5-a]-pyrimidine class of the formula (I).

The pyrimidine derivatives were administered orally to Beagle dogs (body weight approximately 10 kg) either by gastric intubation (with the material in 50 ml of a 12.5% (w/v) 'COMPLAN' suspension) or, when the material was particularly insoluble in water, by means of a gelatine capsule. The Table shows the time within which emesis occurred.

| Derivative of 5-oxo-4,5-dihydro-s-triazolo-[1,5-a] pyrimidine | Dose mg/Dog | Time within which emesis occurred (min) |
|---|---|---|
| 6-methyl-4-n-propyl-2-n-propylamino- | 25 | 30–60 |
| 2-amino-4,6-di-n-propyl- | 25 | 30–60 |
| 2-ethoxycarbonylamino-6-methyl-4-n-propyl- | 25 | 30–60 |
| 2-amino-6-methyl-4-allyl- | 250 | 30–60 |

We claim:

1. A method of avoiding the toxifying effect of a salt of a herbicidal bipyridylium quaternary cation which has been ingested by a human which comprises inducing emesis in said human with consequent removal of the herbicidal salt from said human before lethal amounts of the herbicide can be assimilated by the body, said emesis being induced by administering to said human an emetically effective amount of an emetically active s-triazolo (1,5-a) pyrimidine derivative of the formula:

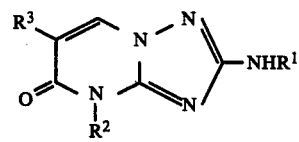

wherein $R^1$ is hydrogen, a $C_{1-4}$ alkyl radical, or a COOEt radical; $R^2$ is a $C_{1-4}$ alkyl radical or an allyl radical, and $R^3$ is a $C_{1-4}$ alkyl radical; or an addition salt thereof.

* * * * *